(12) United States Patent
Lim et al.

(10) Patent No.: US 8,906,044 B2
(45) Date of Patent: Dec. 9, 2014

(54) KNOT PUSHER DEVICE

(75) Inventors: Jyue Boon Lim, New Brighton, MN (US); Raimar Boehlke, Chanhassen, MN (US)

(73) Assignee: St. Jude Medical, Cardiology Division, Inc., Minnetonka, MN (US)

( * ) Notice: Subject to any disclaimer, the term of this patent is extended or adjusted under 35 U.S.C. 154(b) by 452 days.

(21) Appl. No.: 11/551,635

(22) Filed: Oct. 20, 2006

(65) Prior Publication Data

US 2008/0097484 A1    Apr. 24, 2008

(51) Int. Cl.
*A61B 17/04*     (2006.01)
*A61B 17/00*     (2006.01)

(52) U.S. Cl.
CPC ... *A61B 17/0469* (2013.01); *A61B 2017/00371* (2013.01); *A61B 2017/0474* (2013.01); *A61B 2017/0475* (2013.01); *A61B 2017/0477* (2013.01); *A61B 2017/0496* (2013.01)
USPC .......................................... 606/148; 606/144

(58) Field of Classification Search
USPC ................. 606/144, 139, 145–148, 140–143; 112/156, 169; 289/17
See application file for complete search history.

(56) References Cited

U.S. PATENT DOCUMENTS

| | | | | |
|---|---|---|---|---|
| 3,985,138 A | * | 10/1976 | Jarvik | 606/231 |
| 5,084,058 A | * | 1/1992 | Li | 606/148 |
| 5,324,298 A | * | 6/1994 | Phillips et al. | 606/148 |
| 5,364,408 A | | 11/1994 | Gordon | |
| 5,454,820 A | * | 10/1995 | Kammerer et al. | 606/148 |
| 5,458,609 A | | 10/1995 | Gordon et al. | |
| 5,496,348 A | | 3/1996 | Bonutti | |
| 5,540,704 A | * | 7/1996 | Gordon et al. | 606/144 |
| 5,562,684 A | * | 10/1996 | Kammerer | 606/139 |
| 5,643,292 A | | 7/1997 | Hart | |
| 5,741,280 A | * | 4/1998 | Fleenor | 606/148 |
| 5,797,928 A | | 8/1998 | Kogasaka | |
| 5,845,645 A | | 12/1998 | Bonutti | |
| 5,868,762 A | | 2/1999 | Cragg et al. | |
| 5,944,739 A | * | 8/1999 | Zlock et al. | 606/232 |
| 5,984,933 A | * | 11/1999 | Yoon | 606/148 |
| 5,993,459 A | | 11/1999 | Larsen et al. | |
| 6,059,800 A | | 5/2000 | Hart et al. | |

(Continued)

FOREIGN PATENT DOCUMENTS

| | | |
|---|---|---|
| DE | 102004011187 B3 | 9/2005 |
| WO | 95/32669 | 12/1995 |
| WO | 2004/073527 | 9/2004 |

OTHER PUBLICATIONS

PCT International Search Report for International Application No. PCT/US2007/022238, mailed Feb. 18, 2008 (3 pp.).

(Continued)

*Primary Examiner* — Dianne Dornbusch
*Assistant Examiner* — Alexander Orkin
(74) *Attorney, Agent, or Firm* — Holland & Hart

(57) ABSTRACT

A knot pusher device for deploying a plurality of pretied knots to a surgical site is provided. In one embodiment, the knot pusher device comprises a shaft, an inner tubular member, and an inner rod, each having a proximal end and a distal end. The inner tubular member is provided within the shaft and is radially translatable with respect to the shaft. The inner rod is provided within the inner tubular member and is slidably coupled to the inner tubular member and is axially translatable with respect thereto.

18 Claims, 3 Drawing Sheets

(56) References Cited

U.S. PATENT DOCUMENTS

| | | | |
|---|---|---|---|
| 6,074,395 A * | 6/2000 | Trott et al. | 606/104 |
| 6,132,439 A * | 10/2000 | Kontos | 606/139 |
| 6,283,947 B1 | 9/2001 | Mirzaee | |
| 6,358,259 B1 * | 3/2002 | Swain et al. | 606/148 |
| 6,432,115 B1 * | 8/2002 | Mollenauer et al. | 606/148 |
| 6,533,795 B1 | 3/2003 | Tran et al. | |
| 6,702,825 B2 | 3/2004 | Frazier et al. | |
| 6,716,224 B2 * | 4/2004 | Singhatat | 606/148 |
| 6,855,124 B1 | 2/2005 | Gonzalez et al. | |
| 7,160,309 B2 | 1/2007 | Voss | |
| 7,226,467 B2 | 6/2007 | Lucatero et al. | |
| 7,666,196 B1 * | 2/2010 | Miles | 606/144 |
| 2003/0040712 A1 | 2/2003 | Ray et al. | |
| 2003/0181926 A1 * | 9/2003 | Dana et al. | 606/148 |
| 2003/0220659 A1 | 11/2003 | Schmieding et al. | |
| 2004/0068273 A1 | 4/2004 | Fariss et al. | |
| 2004/0097973 A1 | 5/2004 | Loshakove et al. | |
| 2005/0159812 A1 | 7/2005 | Dinger et al. | |
| 2007/0060929 A1 * | 3/2007 | Onishi et al. | 606/139 |
| 2007/0203507 A1 | 8/2007 | McLaughlin et al. | |
| 2008/0033459 A1 | 2/2008 | Shafi et al. | |
| 2008/0097479 A1 | 4/2008 | Boehlke et al. | |
| 2008/0097480 A1 | 4/2008 | Schorr et al. | |
| 2008/0097481 A1 | 4/2008 | Schorr et al. | |
| 2008/0097527 A1 | 4/2008 | Lim et al. | |

OTHER PUBLICATIONS

English Abstract and Machine Translation, DE102004011187, Sep. 29, 2005.

* cited by examiner

KNOT PUSHER DEVICE

FIELD OF THE INVENTION

This invention relates generally to surgical devices, and more specifically to methods and apparatus for advancing surgical knots.

BACKGROUND OF THE INVENTION

Various medical procedures, particularly cardiology procedures, involve accessing a corporeal vessel through the formation of a hole or opening in the vessel wall so that a medical procedure can be performed. After the particular medical procedure has been performed, the access hole in the vessel wall must be closed.

A number of prior vascular closure devices and methods have been developed in an attempt to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. A knot may be tied in the suture to maintain the suture in position closing the hole in the vessel wall. Certain prior closure devices have involved relatively complicated methods and devices for extracting a length of suture from inside the vessel so that the physician can approximate tissue surrounding the hole in the vessel wall through use of the suture.

Typically, a hole in a vessel wall is closed using a sliding knot. The knot can be slid along the suture. Thus, the surgical site is contacted with a sliding suture when the knot is pushed or cinched down and thus causes movement of the suture at the tissue site. Tying of the suture with an over hand suture loop enables sliding of the knot while the suture at the tissue site remains stationary. A device for transporting two or more over hand suture loops to percutaneous surgical site would thus be useful.

BRIEF SUMMARY OF THE INVENTION

Methods and apparatus for advancing surgical knots are provided. More specifically, a knot pusher device for deploying a plurality of pretied knots to a surgical site is provided.

In one embodiment, the knot pusher device comprises a shaft, an inner tubular member, and an inner rod, each having a proximal end and a distal end. The inner tubular member is provided within the shaft and is radially translatable with respect to the shaft. The inner rod is provided within the inner tubular member and is slidably coupled to the inner tubular member and is axially translatable with respect thereto.

In another embodiment, the knot pusher device comprises a suture portion and a handle portion. The suture portion comprises a shaft, an inner tubular member, and an inner rod, each having a proximal end and a distal end. The inner tubular member is provided within the shaft and is radially translatable with respect to the shaft from a first closed position to a second open position. In the first closed position, axial translation of a second suture knot. The inner rod is provided within the inner tubular member and axially translatable with respect thereto. The handle portion includes an actuator assembly and is disposed at the proximal end of the outer shaft. The actuator assembly includes a first actuator coupled to the inner tubular portion and a second actuator coupled to the inner rod.

DETAILED DESCRIPTION OF THE INVENTION

Methods and apparatus for advancing surgical knots are provided. More particularly, a knot pusher device for advancing suture knots at a wound or surgical site is provided. The knot pusher device in accordance with the present invention may be used to transport a plurality of overhand suture loops to a surgical site. It should be appreciated by those skilled in the art, however, that the knot pusher device may be used in conjunction with various types of knots in a variety situations to seal any suitable wound or surgical site.

Generally, to advance overhand suture loops to a surgical site with percutaneous delivery, it is desirable to separate each suture loop during advancement. By providing two loops, the first loop may approximate the wound lips and seal the hole in the vessel and the second loop may secure the sealing result, tightening the knot, and maintaining tightness of the seal during pulsation.

Figure 1:
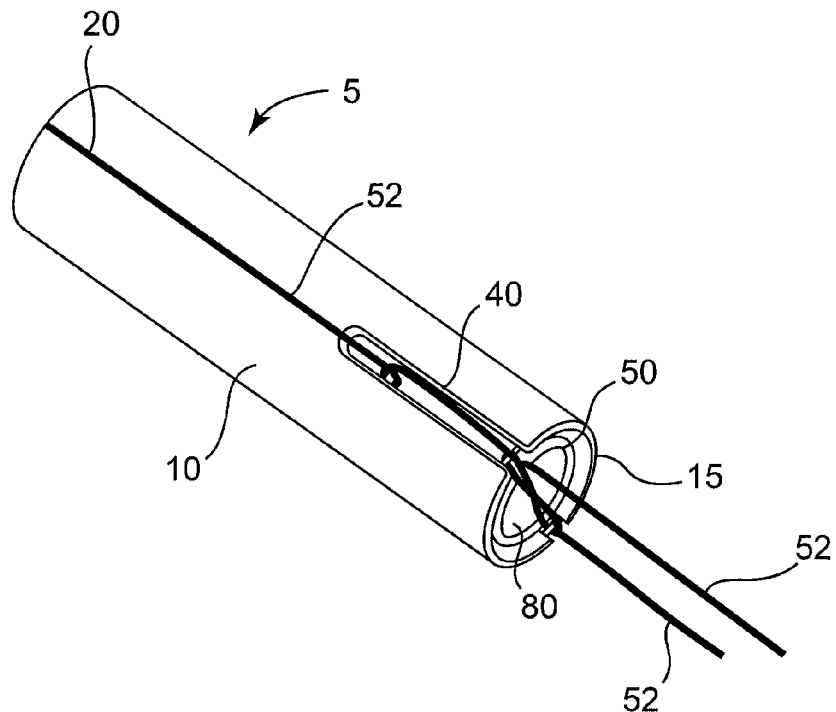
FIG. 1 is a perspective view of the distal end of a knot pusher device in accordance with one embodiment.
Figure 2:
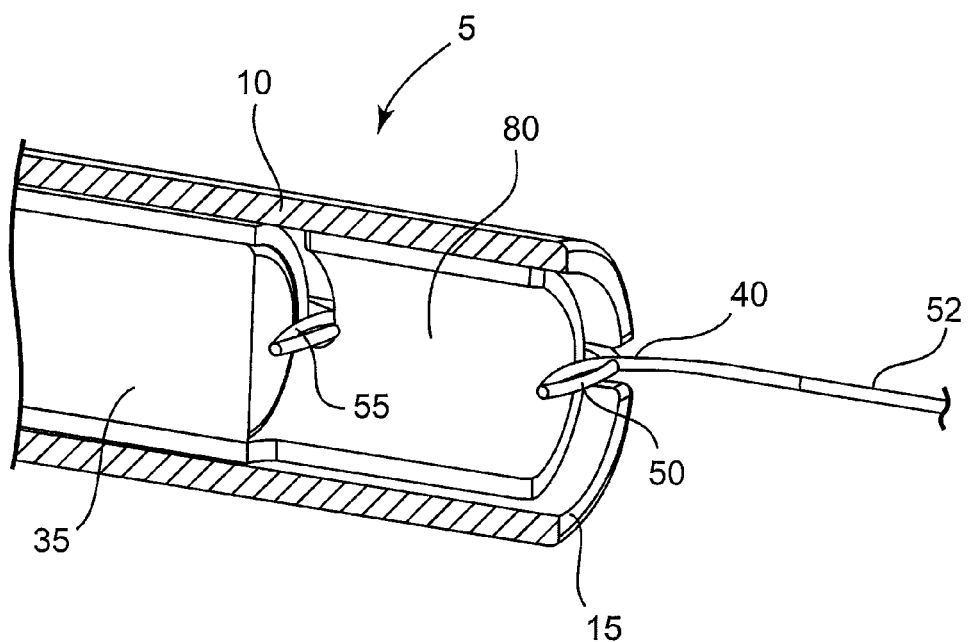
FIG. 2 is a cross sectional view of the device of FIG. 1.
Figure 3:
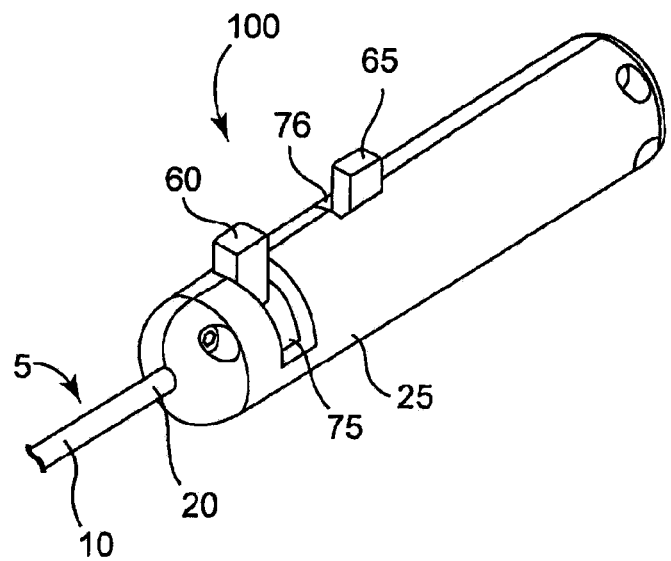
FIG. 3 is a perspective view of an actuator assembly in accordance with one embodiment.
Figure 4:
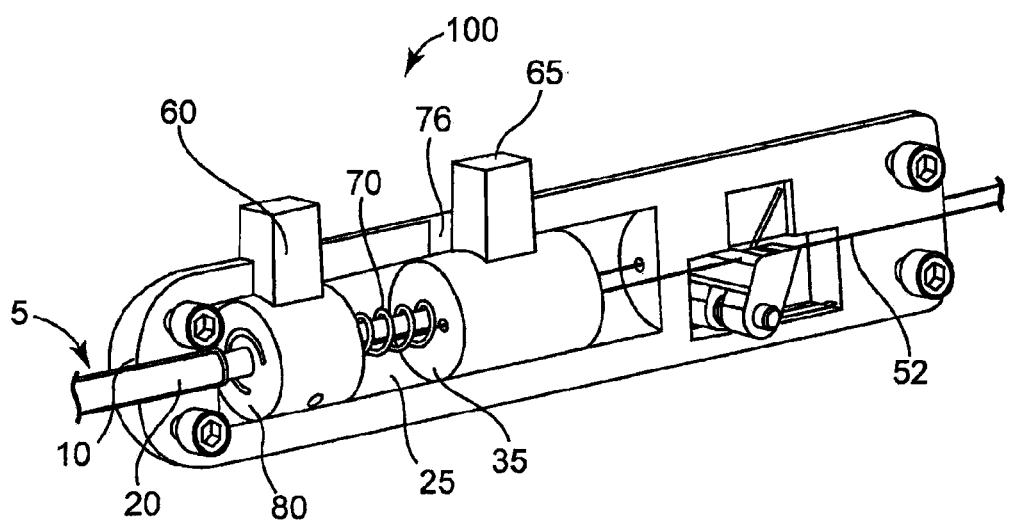
FIG. 4 is a cross sectional view of the device of FIG. 3.

The knot pusher device comprises an suture portion 5, shown in FIGS. 1 and 2, and a handle 100, shown in FIGS. 3 and 4. The suture portion 5 includes an outer shaft 10 having a distal end 15 and a proximal end 20. Generally, as used herein, the term "proximal" refers to towards the surgeon and the term "distal" refers to towards the patient. However, it is to be noted that in some embodiments, the relative position of components of the knot pusher device may be altered. A plurality of suture filaments 52 are provided associated with the suture portion 5.

The outer shaft 10 includes one or more axial passages 40 extending over at least a portion of the length of the outer shaft. As shown, the axial passages 40 begin at the distal end 15 and terminate distally of the proximal end 20. As shown in FIGS. 3 and 4, the proximal end 20 is received by the handle 100. As shown in FIG. 1, the proximal end 20 extends along an exterior of the outer shaft 10 at a location proximal of the axial passage 40.

An inner tubular member 80 is provided within outer shaft 10. The inner tubular member 80 extends substantially from the distal end 15 of the outer shaft 10 to the proximal end 20 of the outer shaft 10. The inner tubular member 80 is generally concentric with the outer shaft 10. In the embodiment shown, the inner tubular member 80 has a semicircular profile along its entire length. In alternative embodiments, the inner tubular member 80 may have varying profiles. The inner tubular member 80 is radially translatable with respect to the outer shaft 10. As can be best seen in FIG. 1, the distal end of the inner tubular member 80 may be slightly recessed from the distal end 15 of the outer shaft 10.

An inner rod 35 may be provided with the inner tubular member 80. The inner rod 35 is axially translatable within the inner tubular member 80. The inner rod 35 may be formed of any suitable material. Softer materials, such as a polymeric material, generally allow for ease of transport along the suture filaments 52 because a lower dynamic friction is caused by the softer inner rod 35 traveling along the suture filament 52. The distal end of inner rod 35 is shown in its fully retracted position in FIG. 2. As shown in FIG. 2, the inner rod 35 has a solid construction.

With particular reference to FIG. 2, the distal end of the outer shaft 10 houses first and second suture knots. The knot pusher device is specifically described with reference to deploying first and second overhand suture loops. However, the knot pusher device may be used for deploying any suture knots and is generally useful for deploying multiple pre-tied knots. In the embodiments shown, the outer shaft 10 houses a first overhand suture loop 50 and a second overhand suture loop 55. In alternative embodiments, the number of suture knots may be more than or less than two. Suture filaments 52 extend from the first and second overhand suture loops 50, 55. FIG. 2 shows the first and second overhand suture loops 50, 55 positioned at axially spaced apart locations within the axial passages 40.

Referring to FIGS. 3 and 4, an actuator assembly 25 is provided with the handle 100. The actuator assembly may be used to affect radial translation of internal tubular member 80 and axial translation of inner rod 35 within the outer shaft 10. The actuator assembly 25 is coupled to the proximal end 20 of the outer shaft 10. The actuator assembly may be configured in any manner suitable for affecting radial translation of the internal tubular member 80 and axial translation of the inner rod 35 to move the first and second overhand suture loops 50, 55 as described below. In the embodiment shown, the actuator assembly 25 comprises a first actuator knob 60 and a second actuator knob 65. The first actuator knob 60 is coupled to the inner tubular member 80 of the suture portion 5. The second actuator knob 65 is coupled to the inner rod 35 of the suture portion 5 and a compression spring 70. As shown, the distal end of the inner rod 35 extends through the compression spring 70.

The inner tubular member 80 can be rotated or radially translated by displacing the first actuator knob 60 radially through a first actuator slot 75. In one embodiment, the inner tubular member 80 can be rotated up to approximately 90 degrees. Prior to rotation, or with the first actuator knob 60 in the position shown in FIG. 3, the inner tubular member 80 is considered in the closed configuration. FIG. 2 illustrates the inner tubular member 80 in the closed position. In the closed position, the inner tubular member 80 prevents axial translation of the second overhand suture loop through the axial passages 40. After rotation, or with the first actuator knob 60 rotated approximately 90 degrees in the first actuator slot, the inner tubular member 80 is considered in the open configuration, described more fully below.

The spring 70 is maintained under compression between the first actuator knob 60 and the second actuator knob 65 such that the second actuator knob 65 remains proximally retracted relative to the inner rod 35. The inner rod 35 may be driven distally, or axially translated, by displacing the second actuator knob 65 axially through a second actuator slot 76. It will be appreciated that a wide variety of other actuator mechanisms could alternatively be used.

Referring again to FIG. 2, the first overhand suture loop 50 and the second overhand suture loop 55 are pre-tied and arranged in the suture portion 5. As a pushing force is applied to the suture portion 5, for example, by manually pushing the suture knot device, including the handle 100 and the suture portion 5, the knots 50, 55 are driven distally toward a surgical site, until the distal end of the suture portion 5 contacts the surgical site, or until force is no longer applied.

Figure 5:
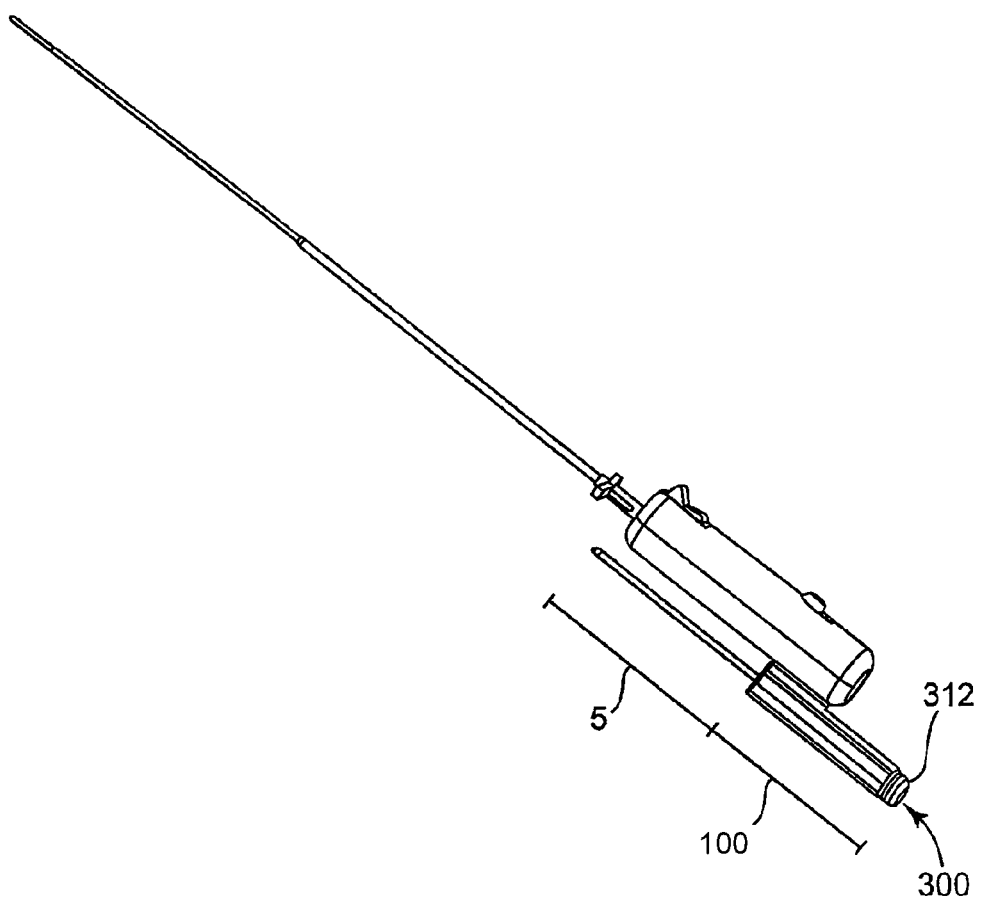
FIG. 5 is a perspective view of a vascular closure delivery device including a suture knot system in accordance with one embodiment.

FIG. 5 illustrates a vascular closure delivery system including the suture knot system 300. As shown, a tensioning knob 312 may be disposed at a proximal end of the handle 100. A suture lock device may be provided at the distal end of the suture portion 5. A suitable suture lock device is taught in copending U.S. applications Ser. Nos. 11/551,523, filed Oct. 20, 2006; and 11/551,642, filed Oct. 20, 2006, entitled "Suture Attachment Device", both herein incorporated by reference. Sutures 52 extend from the surgical site, through the suture portion 5 and, optionally, through the handle 100 to the tensioning knob 312. The sutures travel through the handle 100 and the handle 100 can be used as a pusher to push the suture knots 50, 55. This arrangement keeps the sutures substantially in tension while the suture knots 50, 55 and, optionally, the suture lock device 10, are being deployed. The tensioning knob 312 may additionally be pulled or actuated to affirmatively tense the sutures. By keeping the sutures substantially in tension during knot deployment, slack in the sutures between the suture site and the knots as deployed is substantially avoided.

When the suture portion 5 contacts the surgical site, the first suture loop 50 may be deployed at the surgical site. In embodiments where the first suture loop 50 is a pre-tied knot, the first suture loop 50 is substantially deployed upon contacting the surgical site. To provide a tight and secure knot over the site, forward pressure may be applied to the handle 100 while a tensioning action is applied to the tensioning knob 312. Generally, more pressure applied to the handle 100 and tensioning knob 312 creates more security in the knot. The first suture loop 50 approximates the wound lips and seals the surgical site. Thus, when used to seal an arteriotomy, the first suture loop 50 affects closure of the arteriotomy.

Upon contact of the suture portion 5 with the surgical site, the second overhand suture loop 55 may also be deployed at the surgical site. In one embodiment, deployment of the second overhand suture loop 55 is accomplished by first displacing the first actuator knob 60 radially through the first actuator slot 75. Such actuation causes the inner tubular member 80 to rotate from the closed position to the open position. In the open position, the inner tubular member 80 is aligned with the axial passage 40 such that the second overhand suture loop 55 is free to advance in the distal direction.

The second overhand suture loop 55 is driven in the distal direction by actuation of the second actuator knob 65 axially through the second actuator slot 80. Such actuation causes the inner rod 35 to be driven distally, which, in turn, drives the second overhand suture loop 55 distally through axial passages 40 and out of the suture portion 5 through the lumen 85. The second suture loop 55 secures the sealing result of the first suture loop 50, tightens the knot, and minimizes any loosening of the knot under pulsation.

As previously discussed, during deployment of the knots 50, 55 to the surgical site, it may be desirable to keep the suture filaments 50, 55 in tension. More specifically, it may be desirable to keep the suture filaments at the end of the handle 100 in tension. This can be done by pulling the suture filaments proximally, manually or by using a tensioning knob, while advancing the handle 100 to deliver the knots 50, 55.

In some embodiments, the knot pusher device may be used in conjunction with a vascular closure delivery device such as shown in FIG. 5 and disclosed in copending U.S. patent application Ser. No. 11/551,523, filed Oct. 20, 2006, incorporated herein by reference. In such embodiments, the suture filaments 52 extend to needles of the delivery device. The delivery device deploys the needles and suture filaments 52 at the surgical site. After such deployment, the delivery device may be removed and the knot pusher device kept in place. After deployment of the needles, the suture filaments are in place through the lips of the surgical site. The suture filaments 52 extend proximally and enter the distal tip of the suture portion 5 of the knot pusher device. Thus, after removal of the delivery device, the suture filaments extend from the surgical site back to the knot pusher device, where they are arranged in a pre-tied fashion. The physician can then either close the wound immediately or perform other procedures before closing the wound. Such techniques may be referred to as pre-close techniques wherein the sutures are in place before the wound is dilated to its final size. Thus, the risk of bleeding may be reduced and the wound can be closed simultaneously with retraction of an interventional sheath.

Although the invention has been described with reference to preferred embodiments, persons skilled in the art will recognize that changes may be made in form and detail without departing from the spirit and scope of the invention.

What is claimed is:

1. A knot pusher device for deploying at least one suture knot, the knot pusher device comprising:
    a hollow shaft having a proximal end, a tubular distal end, and at least one shaft slot extending proximally from the tubular distal end and terminating distally of the proximal end along the hollow shaft;
    a hollow inner tubular member positioned within the shaft, the inner tubular member having a proximal end, a distal end, and at least one tube slot, wherein the inner tubular member is rotatable within the shaft between a closed position wherein the inner tubular member holds at least one suture within the at least one shaft slot and the at least one tube slot, and an open position wherein the at least one suture is released to permit removal of the at least one suture from the at least one shaft slot and the at least one tube slot;
    an inner rod positioned within the inner tubular member, the inner rod having a proximal end and a distal end, wherein the inner rod is axially movable within the inner tubular member to deploy the at least one suture from the at least one shaft slot and the at least one tube slot by distally advancing through the inner tubular member.

2. The knot pusher device of claim 1, wherein the inner rod is generally concentric with the shaft.

3. The knot pusher device of claim 1, wherein the inner tubular member comprises a soft polymeric material.

4. The knot pusher device of claim 1, further comprising an actuator assembly disposed at the proximal end of the shaft to facilitate axial movement of the inner rod and rotational movement of the inner tubular member.

5. The knot pusher device of claim 4, wherein the actuator assembly comprises a first actuator to facilitate axial movement of the inner rod and a second actuator to facilitate rotational movement of the inner tubular member.

6. The knot pusher device of claim 1, wherein the device is used to deploy pre-tied overhand suture loops.

7. The knot pusher device of claim 1, wherein the shaft includes a plurality of tube slots to facilitate axial movement of a suture knot in the at least one suture.

8. The knot pusher device of claim 1, wherein the device may be used for pushing and deploying a plurality of suture knots to a surgical site.

9. A knot pusher device for deploying first and second suture knots, the knot pusher device comprising:
    a suture portion comprising:
        a hollow shaft having a proximal end, a tubular distal end, and at least one shaft slot extending proximally from the tubular distal end and terminating distally of the proximal end along the hollow shaft, the first and second suture knots being positioned at axially spaced apart locations within the at least one shaft slot;
        a hollow inner tubular member positioned within the shaft, the inner tubular member having a proximal end, a distal end, and at least one tube slot at least partially aligned with the at least one shaft slot, wherein the inner tubular member is rotatable within the shaft to control release of the first and second knots from the suture portion;
        an inner rod axially movable within the inner tubular member to deploy the first and second suture knots from the suture portion by distally advancing through the inner tubular member.

10. The knot pusher device of claim 9, further comprising a handle portion including an actuator assembly, the handle portion being disposed at the proximal end of the shaft, the actuator assembly including a first actuator operable to rotate the inner tubular portion and a second actuator operable to axially move the inner rod.

11. The knot pusher device of claim 10, wherein the handle further comprises a tensioning knob.

12. The knot pusher device of claim 10, wherein the handle further comprises a compression spring, the second actuator being coupled to the compression spring and the inner tubular member extending through the compression spring.

13. The knot pusher device of claim 9, wherein a suture filament extends from the distal end of the inner tubular member, through the inner tubular member, out of the proximal end of the inner tubular member, into the handle, and to a tensioning knob.

14. The knot pusher device of claim 9, wherein the inner tubular member rotates through approximately 90 degrees.

15. The knot pusher device of claim 9, wherein at least one of the first and second suture knots are positioned within the at least one tube slot.

16. The knot pusher device of claim 9, wherein the inner tubular portion is rotatable between a first position holding at least one of the first and second suture knots within the shaft slot and the tube slot, and a second position wherein the first and second suture knots are released for removal from the shaft slot and the tube slot.

17. The knot pusher device of claim 9, wherein the inner rod has a solid construction.

18. The knot pusher device of claim 9, further comprising at least one suture having at least one of the first and second suture knots, the at least one suture extending outside of the shaft at a location proximal of the shaft slot.

* * * * *